US012692034B2

(12) United States Patent
Statham et al.

(10) Patent No.: US 12,692,034 B2
(45) Date of Patent: *Jul. 28, 2026

(54) STERILIZATION PACKAGING

(71) Applicant: STERIS Corporation, Mentor, OH (US)

(72) Inventors: Samantha Statham, Philadelphia, PA (US); Amrita Singh, Drexel Hill, PA (US); Renee Buthe, Holmes, PA (US); Aaron Mertens, Milwaukee, WI (US); Lisa Chen, Philadelphia, PA (US)

(73) Assignee: STERIS Corporation, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/351,648

(22) Filed: Oct. 7, 2025

(65) Prior Publication Data

US 2026/0035116 A1    Feb. 5, 2026

Related U.S. Application Data

(63) Continuation of application No. 18/775,311, filed on Jul. 17, 2024, now Pat. No. 12,466,597.

(60) Provisional application No. 63/515,015, filed on Jul. 21, 2023.

(51) Int. Cl.
| | |
|---|---|
| *B65D 75/30* | (2006.01) |
| *A61B 50/30* | (2016.01) |
| *A61L 2/07* | (2006.01) |
| *B65B 55/02* | (2006.01) |
| *B65D 33/04* | (2006.01) |
| *B65D 33/28* | (2006.01) |
| *D04H 1/4291* | (2012.01) |

| | |
|---|---|
| *D04H 1/56* | (2006.01) |
| *A61L 103/15* | (2026.01) |

(52) U.S. Cl.
CPC ............... *B65B 55/02* (2013.01); *A61L 2/07* (2013.01); *B65D 33/04* (2013.01); *B65D 33/28* (2013.01); *D04H 1/4291* (2013.01); *D04H 1/56* (2013.01); *A61L 2103/15* (2026.01); *D10B 2401/20* (2013.01); *D10B 2505/10* (2013.01); *D10B 2509/00* (2013.01)

(58) Field of Classification Search
CPC ........ B65D 33/04; B65D 33/28; B65D 75/12; B65D 75/522; B65B 55/02; B32B 27/10; B32B 29/00; A61L 2/07; A61L 2202/24; D10B 2401/02; D10B 2505/10; D10B 2509/00
USPC .......... 206/363, 438, 776–782; 383/61.4, 72, 383/106
See application file for complete search history.

(56) References Cited

U.S. PATENT DOCUMENTS

| | | | | |
|---|---|---|---|---|
| 2005/0268573 | A1* | 12/2005 | Yan | A61L 2/26 206/439 |
| 2016/0311567 | A1* | 10/2016 | Nakamura | B65B 55/18 |
| 2016/0347492 | A1* | 12/2016 | Lu | B65B 7/02 |

* cited by examiner

*Primary Examiner* — Luan K Bui
(74) *Attorney, Agent, or Firm* — Schwegman Lundberg & Woessner, P.A.

(57) ABSTRACT

Various aspects disclosed relate to a sterilization packaging. The sterilization packaging includes a first major surface that is substantially opaque. The sterilization packaging further includes a second major surface. The sterilization packaging further includes an opaque portion and a substantially transparent portion.

20 Claims, 5 Drawing Sheets

STERILIZATION PACKAGING

CROSS-REFERENCE TO RELATED APPLICATION

This application is a continuation of U.S. patent application Ser. No. 18/775,311, filed Jul. 17, 2024, which claims the benefit of priority to U.S. Provisional Patent Application Ser. No. 63/515,015 entitled "STERILIZATION PACKAG-ING," filed Jul. 21, 2023, the disclosure of each of which are incorporated herein in their entirety by reference.

BACKGROUND

Sterilization of medical instruments, dental instruments, and/or pharmaceutical instruments is crucial to ensure patient safety. When instruments or pharmaceuticals come into contact with a patient's body, they can potentially introduce harmful microorganisms, such as bacteria, viruses, and fungi. Sterilization eliminates these microorganisms, reducing the risk of infection or cross-contamination during medical procedures.

SUMMARY OF THE INVENTION

Various aspects disclosed relate to a sterilization packaging. The sterilization packaging includes a first major surface that is substantially opaque. The sterilization packaging further includes a second major surface. The sterilization packaging further includes an opaque portion and a substantially transparent portion.

BRIEF DESCRIPTION OF THE FIGURES

The drawings illustrate generally, by way of example, but not by way of limitation, various aspects of the present invention.

DETAILED DESCRIPTION OF THE INVENTION

Figure 1:
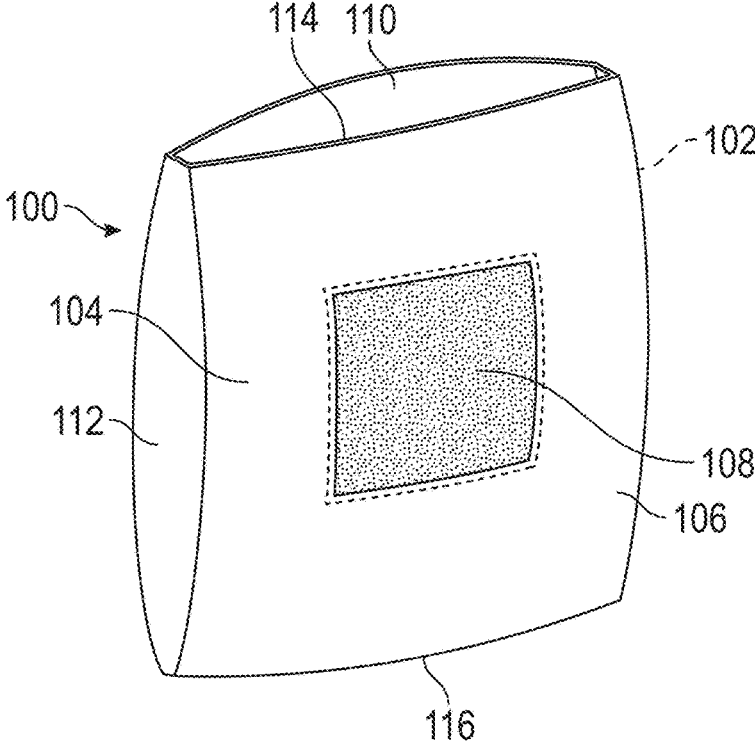
FIG. 1 is a perspective view of a sterilization packaging, in accordance with various aspects.
Figure 2:
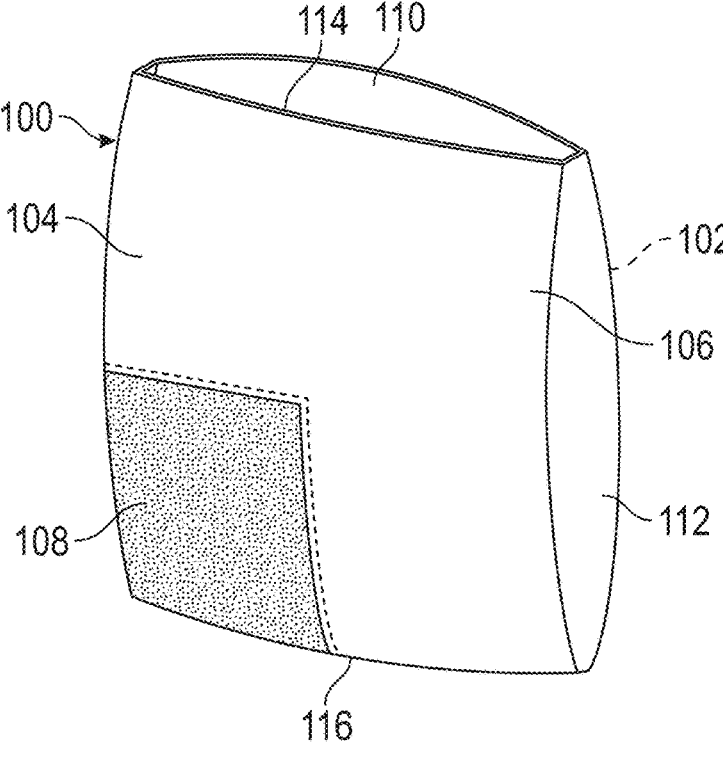
FIG. 2 is a perspective view of another sterilization packaging, in accordance with various aspects.
Figure 3:
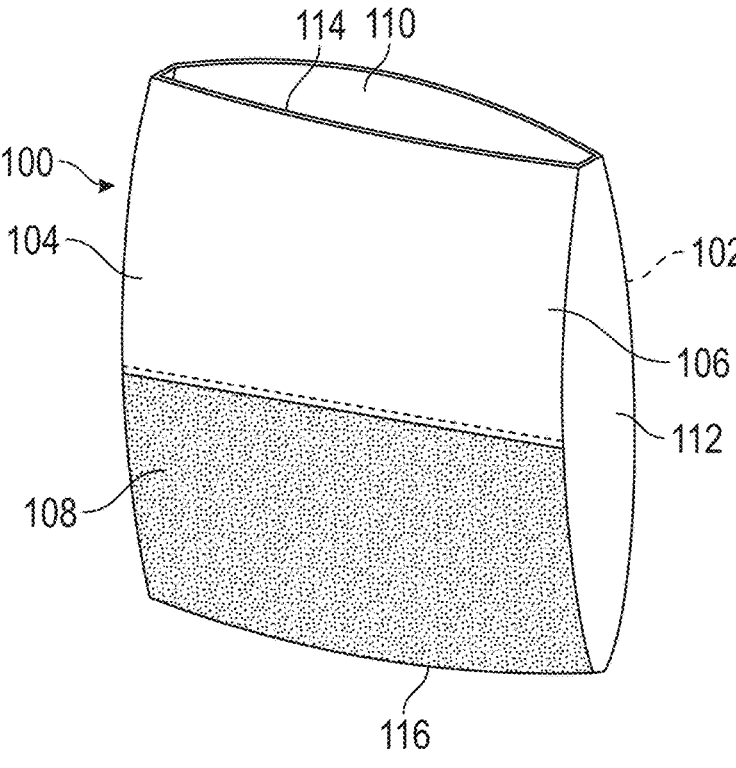
FIG. 3 is a perspective view of another sterilization packaging, in accordance with various aspects.
Figure 4:
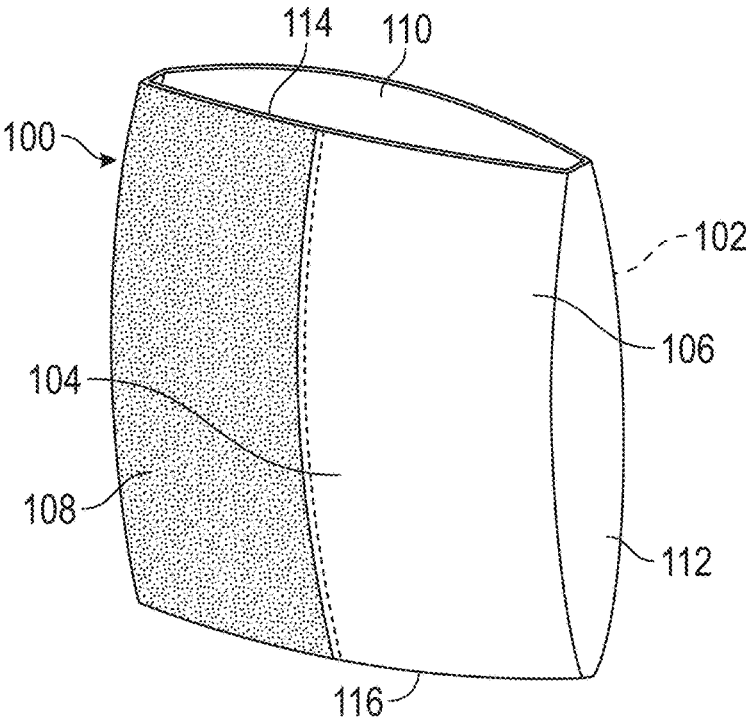
FIG. 4 is a perspective view of another sterilization packaging, in accordance with various aspects.
Figure 5:
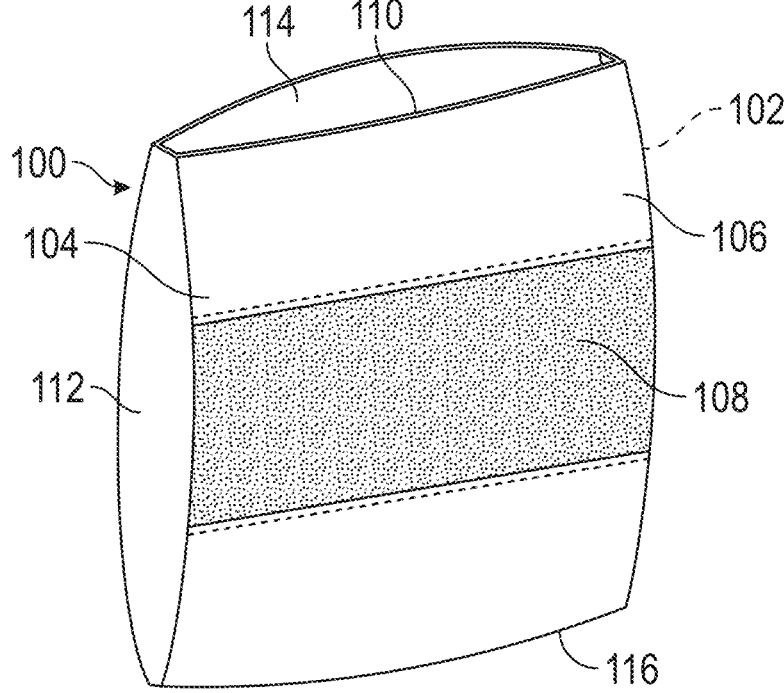
FIG. 5 is a perspective view of another sterilization packaging, in accordance with various aspects.
Figure 6:
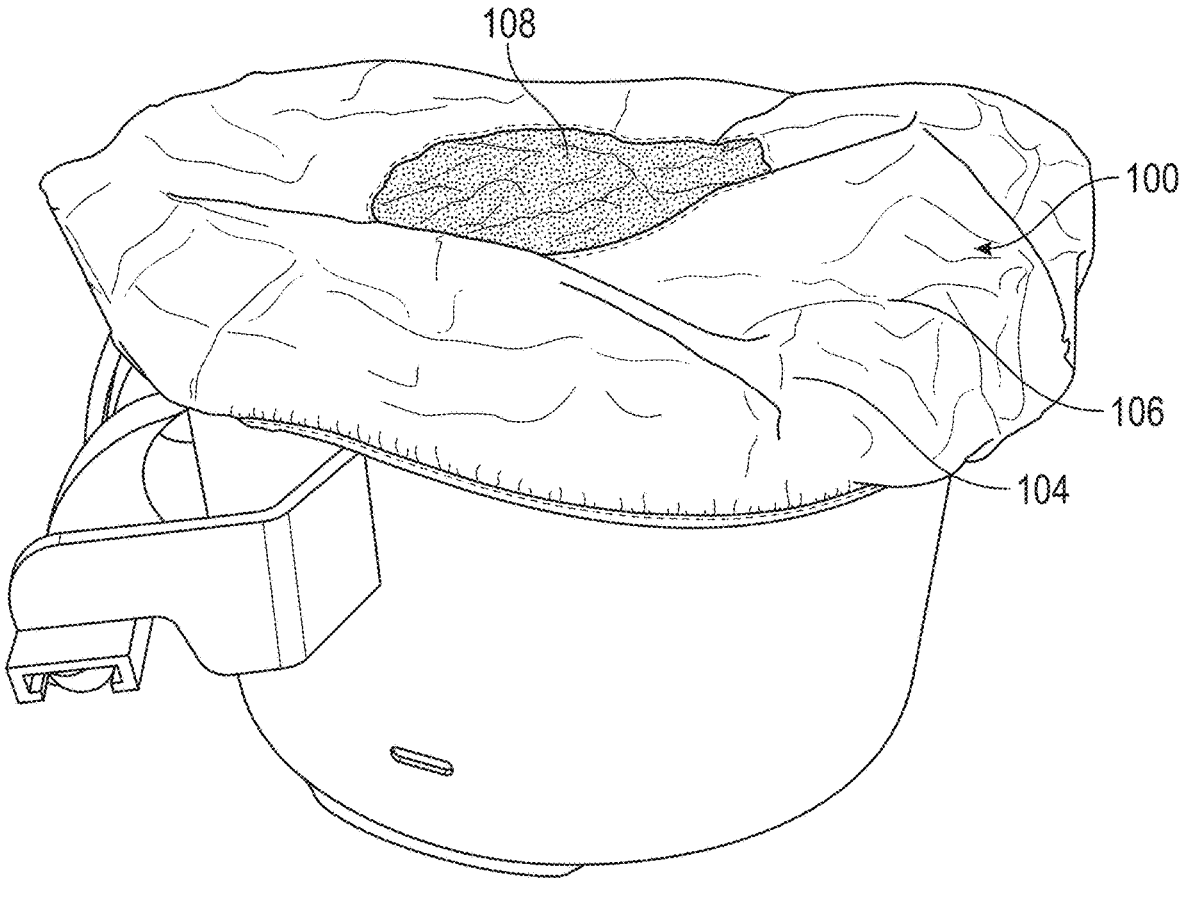
FIG. 6 is a perspective view of another sterilization packaging, in accordance with various aspects.

Reference will now be made in detail to certain aspects of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

According to various aspects of the instant disclosure a sterilization packaging is provided. In some aspects, the sterilization packaging takes the form of a closable and/or scalable bag. FIGS. 1-7B show examples of sterilization packaging 100. FIGS. 1-7B show many of the same components with common reference numbers and are discussed concurrently.

As shown, sterilization packaging includes first major surface 102 and second major surface 104. First major surface 102 and second major surface 104 can be joined directly along a seam. In other examples first major surface 102 and second major surface 104 can be joined by a joining surface, such as joining surface 112. First major surface 102 and joining surface 112 are opaque. That is visible light is not transmitted therethrough. Second major surface 104, as shown, includes two portions. Those portions are opaque portion 106 and substantially transparent portion 108.

First major surface 102 and opaque portion 106 of second major surface 104 can include a naturally opaque polymeric material non-limiting examples of such polymeric materials include a polyolefin, a cellulose, or a combination thereof. As a specific example, the polyolefin is a nonwoven spun-bond polyolefin. If the material is not naturally opaque, pigments, colorings, or the like can be incorporated in the material to make it opaque. First major surface 102 and opaque portion 106 can be same material or mixture of materials. But in some examples, it is possible for them to include different materials.

Substantially transparent portion 108 includes a material that has some degree of transparency. That is visible light is at least partially visible therethrough. Examples of suitable materials for substantially transparent portion 108 includes a polypropylene, a polyurethane, a polyethylene, or a combination thereof. Examples of suitable polyethylenes include a low-density polyethylene or a high-density polyethylene. Substantially transparent portion 108 can include additives such as an antioxidant, a stabilizer, an antifogging compound, or a combination thereof.

As shown in FIGS. 1-7B, substantially transparent portion 108 does not account for 100% total surface area of second major surface 104. According to various examples, substantially transparent portion 108 can range from about 10% total surface area of second major surface 108 to about 80% total surface area of second major surface 108, about 15% total surface area of second major surface 108 to about 35% total surface area of second major surface 108, less than, equal to, or greater than about 10% total surface area of second major surface 108, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80% total surface area of second major surface 108.

As shown, substantially transparent portion 108 is continuous. That is substantially transparent portion 108 is not broken by any opaque material. In alternative examples substantially transparent portion 108 can be discontinuous. That is substantially transparent portion 108 can exist in multiple sections broken by opaque portions.

In some examples, it is possible for transparent portion 108 to expand to first major surface 102. Additionally, in some examples second major surface can include its own substantially transparent portion having any of the properties, materials, or the like described herein with respect to substantially transparent portion 108.

FIGS. 1-7B show that substantially transparent portion 108 can take on many different shapes or be a many different locations. For example, substantially transparent portion 108 can have a rounded (e.g., circular or ovular) profile, a rectangular profile, a square profile, or a triangular profile. Any other polygonal profile. Substantially transparent portion 108 can be elongated such that it extends generally in a direction between first end 114 and second end 116.

Figure 7B:
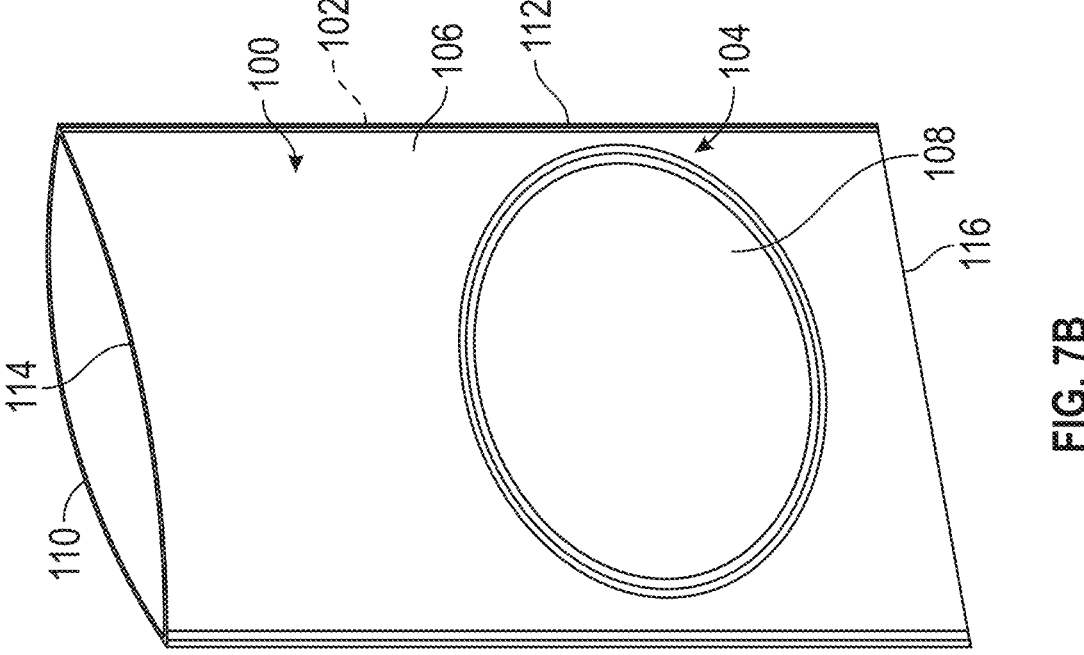
FIG. 7B is a perspective view of another sterilization packaging, in accordance with various aspects.
Figure 7A:
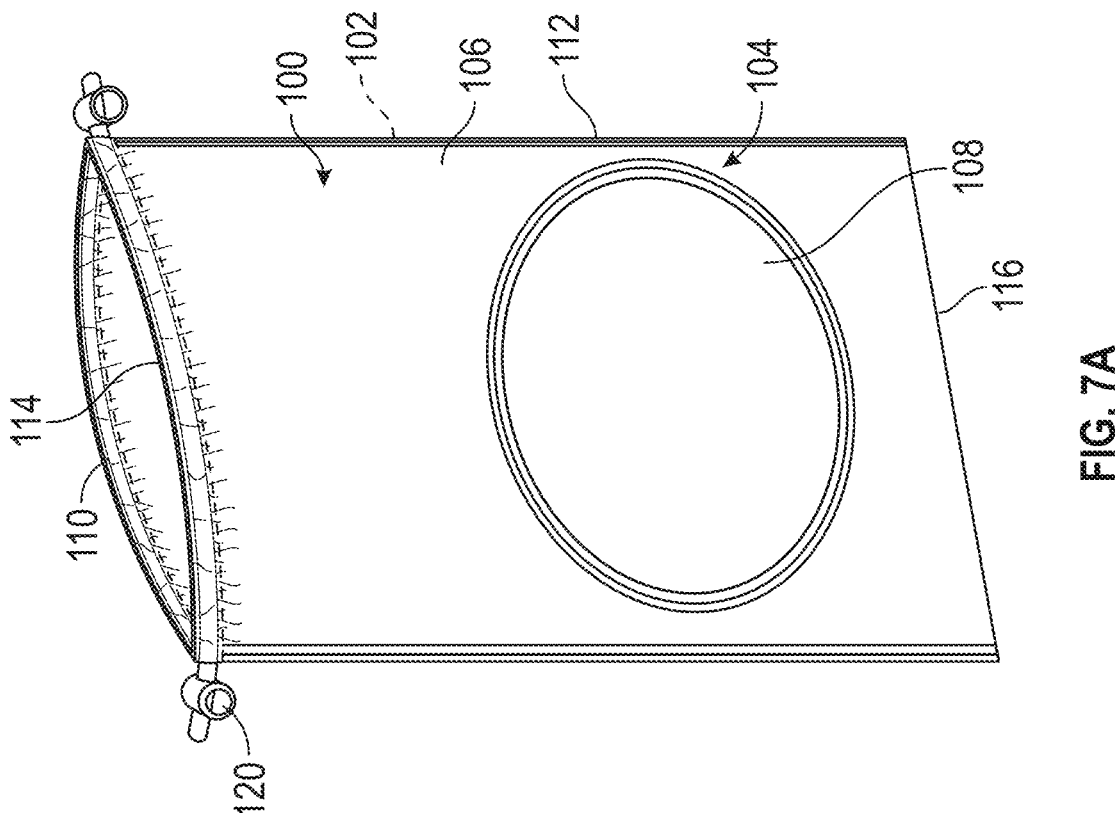
FIG. 7A is a perspective view of another sterilization packaging, in accordance with various aspects.

As shown, first end 114 is open. First end 114 can be sealed with an adhesive or closed with a mechanical device such as an elastic band or a drawstring. For example, FIG. 7A shows drawstring 120 closing first end 114.

In operation, a device is located within or at least partially covered by sterilization packaging 100. The instrument can take on many different forms. For example, the instrument can be a pharmaceutical instrument or a medical instrument. Pharmaceutical instruments generally include instruments used to manufacture pharmaceuticals. General examples of pharmaceutical instruments include quality monitoring equipment, environmental monitoring equipment and parts, testing equipment, clean room supplies, clean room equipment, glassware, purification equipment, filters, housings, chutes, tracks, rails, star wheels, bowls, hoppers, tubing, needles, fittings, clamps, gaskets, and assembly line equipment.

Medical instruments can include various devices used by a physician, physician's assistant, nurse, medical assistant, or the like. Medical instruments can also include dental instruments used by a dentist or dental hygienist.

Non-limiting examples of dental instruments include, dental mirrors, dental probes, scalers, curettes, dental forceps, elevators, dental burs, dental drill bits, dental syringes, excavators, amalgam carriers, composite placement instruments, dental tweezers, retractors, crown removers, orthodontic instruments (e.g., Band Pushers, Pliers), endodontic instruments (e.g., Files, Reamers, Obturators), periodontal instruments (e.g., Periodontal Probes, Curettes), implant instruments (e.g., Implant Drivers, Abutment Removal Tools), rubber dam instruments (e.g., Rubber Dam Clamps, Frame Assemblies), and sterilization trays and cassettes (used to hold and organize various dental instruments during the sterilization process).

Non-limiting examples of medical instruments include surgical scissors, forceps (e.g., Hemostats, Tissue Forceps), scalpels, retractors, needle holders, surgical clamps (e.g., Bulldog Clamps, Kocher Clamps), specula (e.g., Nasal Specula), trocars, dilators, biopsy punches, curettes, bone chisels, rongeurs, surgical suction tubes, surgical drills and burrs, ophthalmic instruments (e.g., Eye Scissors, Retractors, Speculums), endoscopic instruments (e.g., Laparoscopic Graspers, Scissors, Trocars), and microsurgical instruments (e.g., Micro Scissors, Micro Forceps).

The medical instrument, dental instrument, and/or pharmaceutical instrument and sterilization packaging is able to be used in conjunction with a steam autoclave. Steam autoclaving is a highly effective method for sterilizing objects using high-pressure steam. It works by subjecting the objects to a combination of high temperature and pressure, which eradicates any microorganisms present, including bacteria, viruses, and fungi. In general, steam autoclaving includes the following steps:

1. Loading: The objects to be sterilized are placed inside the autoclave chamber, typically on racks or trays. These objects can include laboratory glassware, surgical instruments, pharmaceutical equipment, medical equipment, or other heat-resistant materials. Once the objects are loaded, the autoclave door is securely sealed.
2. Steam Source: The autoclave is a sealable, leak free system that is connected to a steam source, which supplies steam to the autoclave and jacket.
3. Air Removal: Air is removed from the autoclave chamber and associated piping either using pre-vacuum pulses or gravity displacement process. During pre-vacuum pulses, air is actively removed via a series of steam pulses. The chamber is alternately depressurized using a vacuum pump/water ejector system and pressurized with steam. For gravity displacement, air is forced out of the chamber through the drain, steam traps and/or steam bleeds as steam enters the autoclave.
4. Heating: The heating process begins by injecting steam, and the temperature inside the chamber is gradually raised. Most autoclaves operate at temperatures between 121° C. (250° F.) and 134° C. (273° F.).

5. Pressure Build-up: As steam is injected into the auto-clave, pressure builds and the temperature rises. The pressure can range from 15 to 30 pounds per square inch (psi) above atmospheric pressure, depending on the desired sterilization conditions.

6. Sterilization Phase: The combination of high tempera-ture and pressure is lethal to microorganisms. The steam penetrates the objects being sterilized, effectively killing any bacteria, viruses, or other pathogens pres-ent. This phase typically lasts for a specified duration, which can vary depending on the load, size, and type of objects being sterilized. It ensures thorough steriliza-tion of the objects.

7. Depressurization: After the sterilization phase is com-plete, the autoclave begins to depressurize. Depressur-ization can be immediate, using a post-sterilization vacuum or gradual by venting through filters.

8. Drying: Once the pressure has been released, the autoclave enters the drying phase. During this phase, filtered hot air is circulated within the chamber to remove any residual moisture from the sterilized objects.

9. Cooling: After drying, the autoclave initiates the cool-ing process. Cool filtered air is injected into the auto-clave until the desired temperature is achieved, ensur-ing the objects can be safely handled without the risk of thermal damage.

10. Unloading: Once the cooling process is complete, the autoclave door can be safely opened. The sterilized objects are removed from the chamber and are now ready for use in an aseptic environment.

Given the temperatures used during steam autoclaving the melting point or glass transition temperature of a material of first major surface 102 and second major surface 104 is less than or equal to 135° C., less than or equal to 130° C., less than or equal to 125° C. or in a range of from about 120° C. to about 140° C. or 125° C. to 135° C.

A particular advantage of the instantly claimed construc-tion is that substantially transparent portion 108 can be included while allowing sterilization packaging 100 to be used at the temperatures associated with steam autoclaving. Traditionally, substantially transparent materials do not have particularly high melting temperatures or glass transition temperatures. Therefore, including substantially transparent materials can weaken sterilization packaging 100 or prevent it from retaining steam. However, the instantly disclosed sterilization packaging 100 strikes a balance of including more of the tougher opaque material of first major surface 102 and second major surface 104.

With this the overall durability of sterilization packaging 100 is increased and the ability to retain steam within sterilization packaging 100 is increased. Additionally, sub-stantially transparent materials tend to not be "breathable" (e.g., allow steam from the autoclave to pass therethrough). However, the opaque material of first major surface 102 and second major surface 104 is breathable. Therefore, by mini-mizing the size of the substantially transparent portion 108 and maximizing the size of the opaque material—all while still allowing for visual inspection of the instrument allows the sterilization of the instrument to be increased. Addition-ally, including substantially transparent portion 108 allows for inspection of the instrument to ensure that it is substan-tially dry. Once the instrument is confirmed to be substan-tially dry, the instrument can be removed for use.

It has been found that sizing substantially transparent portion 108 to be in a range of from about 30% total surface area of first major surface 102 to about 40% total surface area of first major surface 102, about 33% total surface area of first major surface 102 to about 37% total surface area of first major surface 102, less than, equal to, or greater than about 30% total surface area of first major surface 102, 31, 32, 33, 34, 35, 36, 37, 38, 39, or about 40% total surface area of first major surface 102 is particularly advantageous. That is sizing transparent portion 108 in that range allows for the maximum amount of breathability for steam to penetrate sterilization packaging 100 while allowing for substantially transparent portion 108 to be large enough for a visual inspection of the instrument located therein or at least partially covered by sterilization packaging 100.

Sterilization packaging 100 can be made using any num-ber of suitable techniques. As an example, the opaque material can be cut into two pieces to form first major surface 102 and second major surface 104. The substantially transparent material is also cut to size. A void is formed in the opaque material and the substantially transparent mate-rial is placed in the void and heat sealed to the opaque material of second major surface 104.

First major surface 102 and second major surface 104 are then head sealed to each other and excess material (if present) are removed. If a drawstring is incorporated to close first end 110, the corners at first end 110 are cut at about a 45 degree angle the edges are hemmed with a drawstring being inserted therein.

Exemplary Aspects

The following exemplary aspects are provided, the num-bering of which is not to be construed as designating levels of importance:

Aspect 1 provides a sterilization packaging comprising:
a first major surface that is substantially opaque;
a second major surface comprising:
an opaque portion; and
a substantially transparent portion.

Aspect 2 provides the sterilization packaging of Aspect 1, wherein the first major surface and the opaque portion of the second major surface comprise a polyolefin, a cellulose, or a combination thereof.

Aspect 3 provides the sterilization packaging of Aspect 2, wherein the polyolefin is a nonwoven spunbond polyolefin.

Aspect 4 provides the sterilization packaging of any of Aspects 1-3, wherein the substantially transparent portion comprises a polypropylene, a polyurethane, a polyethylene, or a combination thereof.

Aspect 5 provides the sterilization packaging of Aspect 4, wherein the polyethylene is a low-density polyethylene or a high-density polyethylene.

Aspect 6 provides the sterilization packaging of any of Aspects 1-5, wherein the substantially transparent portion comprises about 10% total surface area of the second major surface to about 80% total surface area of the second major surface.

Aspect 7 provides the sterilization packaging of any of Aspects 1-6, wherein the substantially transparent portion comprises about 15% total surface area of the second major surface to about 35% total surface area of the second major surface.

Aspect 8 provides the sterilization packaging of any of Aspects 1-7, wherein the substantially transparent portion is continuous.

Aspect 9 provides the sterilization packaging of any of Aspects 1-8, wherein the substantially transparent portion is discontinuous.

Aspect 10 provides the sterilization packaging of any of Aspects 1-9, wherein the substantially transparent portion has an elongated profile.

Aspect 11 provides the sterilization packaging of Aspect 10, wherein the substantially elongated profile extends horizontally from a first end to a second end of the sterilization packaging.

Aspect 12 provides the sterilization packaging of any of Aspects 1-11, wherein the substantially transparent portion has a rounded profile, a rectangular profile, a square profile, or a triangular profile.

Aspect 13 provides the sterilization packaging of any of Aspects 1-12, wherein the substantially transparent portion further comprises an antioxidant, a stabilizer, an antifogging compound, or a combination thereof.

Aspect 14 provides the sterilization packaging of any of Aspects 1-13, wherein the substantially transparent portion is further disposed on the first major portion.

Aspect 15 provides the sterilization packaging of any of Aspects 1-14, further comprising a drawstring.

Aspect 16 provides the sterilization packaging of any of Aspects 1-15, further comprising a medical instrument disposed therein.

Aspect 17 provides the sterilization packaging of any of Aspects 1-16, further comprising a pharmaceutical instrument disposed therein.

Aspect 18 provides the sterilization packaging of any of Aspects 1-17, wherein a melting point or glass transition temperature of a material of the first major portion and second major portion is less than or equal to 135° C.

Aspect 19 provides the sterilization packaging of any of Aspects 1-18, wherein a melting point or glass transition temperature of a material of the first major portion and second major portion is less than or equal to 130° C.

Aspect 20 provides the sterilization packaging of any of Aspects 1-19, wherein the packaging is a sealed or closable bag.

Aspect 21 provides the sterilization packaging of any of Aspects 1-19, wherein the packaging comprises an open end defined by the first major portion, the second major portion, or both.

Aspect 22 provides the sterilization packaging of Aspect 21, further comprising an elastic band disposed about the open end.

Aspect 23 provides a method of making the sterilization packaging of any of Aspects 1-19, the method comprising:
  adhering the first major surface and the second major surface; and
  adhering the substantially transparent portion to the second major surface.

Aspect 24 provides the method of Aspect 23, wherein adhering is accomplished by heat sealing, ultrasonic welding, infrared welding, forming a double seal, or a combination thereof.

Aspect 25 provides a method of sterilizing an instrument, the method comprising:
  contacting the sterilization packaging of any of Aspects 1-21, with steam, wherein a medical instrument is located within the sterilization packaging.

Aspect 26 provides the method of Aspect 25, wherein the sterilization packaging is contacted with steam in an autoclave.

Aspect 27 provides the method of any of Aspects 25 or 23, further comprising disposing the medical instrument within the sterilization packaging.

Aspect 28 provides the method of any of Aspects 25-24, wherein the steam is at a temperature of 135° C. or less.

Aspect 29 provides the method of any of Aspects 25-25, wherein the steam is at a temperature of 130° C. or less.

Aspect 30 provides the method of any of Aspects 25-26, further comprising visually inspecting the medical instrument through the substantially transparent portion to confirm that the medical instrument is substantially dry.

Aspect 31 provides the method of Aspect 30, further comprising removing the medical instrument from the sterilization packaging upon confirming that that medical instrument is substantially dry.

Aspect 32 provides the method of any of Aspects 25-31, wherein the instrument is
  a medical instrument, pharmaceutical instrument, or a dental instrument.

What is claimed is:

1. A sterilization packaging comprising:
  a first major surface that is substantially opaque and steam-permeable;
  an opposed second major surface joined to the first major surface and comprising an opaque steam-permeable portion; and
  a substantially transparent portion comprising about 10% total surface area of the second major surface to about 80% total surface area of the second major surface, the substantially transparent portion joined to the opaque portion by a heat seal, an ultrasonic weld, an infrared weld, or a combination thereof;
  wherein the substantially transparent portion further comprises an antioxidant, a stabilizer, an antifogging compound, or a combination thereof and is capable of maintaining substantial transparency when exposed to steam at a sterilization temperature of at least 121° C.

2. The sterilization packaging of claim 1, wherein the substantially transparent portion comprises about 35% total surface area of the second major surface to about 80% total surface area of the second major surface.

3. The sterilization packaging of claim 1, wherein the substantially transparent portion comprises about 60% total surface area of the second major surface to about 80% total surface area of the second major surface.

4. The sterilization packaging of claim 1, wherein the first major surface and the opaque portion of the second major surface comprise a steam-permeable nonwoven spunbond polyolefin.

5. The sterilization packaging of claim 1, wherein the substantially transparent portion comprises a steam-resistant polyethylene that maintains transparency at sterilization temperatures up to 135° C.

6. The sterilization packaging of claim 1, wherein the substantially transparent portion has a rectangular profile or a rounded profile and extends continuously across a majority of the second major surface.

7. The sterilization packaging of claim 1, wherein the substantially transparent portion is positioned to provide visual access to at least 70% of an interior space of the sterilization packaging.

8. The sterilization packaging of claim 1, further comprising a medical instrument or a pharmaceutical manufacturing equipment disposed therein, and wherein the substantially transparent portion allows a user to make visual confirmation that the medical instrument or the pharmaceutical manufacturing equipment is substantially dry following steam sterilization.

9. The sterilization packaging of claim 1, wherein the packaging is configured as a closable bag with an open end, and further comprising a drawstring disposed about the open end.

10. The sterilization packaging of claim 1, wherein the first major surface and the opaque portion of the second major surface comprise a polyolefin, a cellulose, or a combination thereof.

11. The sterilization packaging of claim 5, wherein the steam-resistant polyethylene maintains transparency at sterilization temperatures up to 140° C.

12. The sterilization packaging of claim 1, wherein the substantially transparent portion comprises about 70% total surface area of the second major surface to about 80% total surface area of the second major surface.

13. The sterilization packaging of claim 1, wherein the antioxidant, stabilizer, or antifogging compound prevents condensation buildup during steam exposure at sterilization temperatures.

14. The sterilization packaging of claim 1, wherein the substantially transparent portion comprises a polypropylene, a polyurethane, a polyethylene, or a combination thereof.

15. The sterilization packaging of claim 14, wherein the polyethylene is a low-density polyethylene or a high-density polyethylene.

16. The sterilization packaging of claim 8, wherein the substantially transparent portion enables visual confirmation of complete drying of internal surfaces of the medical instrument or the pharmaceutical manufacturing equipment following steam sterilization.

17. The sterilization packaging of claim 1, wherein the substantially transparent portion has a rounded profile, a rectangular profile, a square profile, or a triangular profile.

18. The sterilization packaging of claim 1, wherein a melting point or glass transition temperature of a material of the first major portion and second major portion is less than or equal to 135° C.

19. A method of sterilizing a medical instrument or the pharmaceutical manufacturing equipment comprising:

placing the medical instrument or the pharmaceutical manufacturing equipment in the sterilization packaging of claim 8;

sealing the sterilization packaging;

exposing the sealed sterilization packaging to steam at a temperature of at least 121° C.; and visually inspecting the medical instrument or the pharmaceutical manufacturing equipment through the substantially transparent portion to confirm sterilization completion.

20. The method of claim 19, wherein the steam is at a temperature of 135° C. or less.

\* \* \* \* \*